(12) United States Patent
Stenton et al.

(10) Patent No.: US 8,061,917 B2
(45) Date of Patent: Nov. 22, 2011

(54) LIQUID APPLICATOR AND METHOD OF USE

(75) Inventors: Richard J. Stenton, Horrabridge (GB); George Reed, Plymouth (GB)

(73) Assignee: MedLogic Global Limited, Plymouth, Devon (GB)

( * ) Notice: Subject to any disclaimer, the term of this patent is extended or adjusted under 35 U.S.C. 154(b) by 514 days.

(21) Appl. No.: 11/450,659

(22) Filed: Jun. 8, 2006

(65) Prior Publication Data
US 2007/0147947 A1    Jun. 28, 2007

Related U.S. Application Data

(60) Provisional application No. 60/689,696, filed on Jun. 10, 2005.

(51) Int. Cl.
*B43K 5/14* (2006.01)
(52) U.S. Cl. .............................. 401/134; 401/133; 604/3
(58) Field of Classification Search .......... 401/133–135, 401/196, 132, 205; 604/3
See application file for complete search history.

(56) References Cited

U.S. PATENT DOCUMENTS

| | | | |
|---|---|---|---|
| 2,784,127 A | 3/1957 | Joyner et al. | |
| 3,527,224 A | 9/1970 | Rabinowitz | |
| 3,591,676 A | 7/1971 | Hawkins et al. | |
| 3,667,472 A | 6/1972 | Halpern | |
| 3,995,641 A | 12/1976 | Kronenthal et al. | |
| 4,035,334 A | 7/1977 | Davydov et al. | |
| 4,038,345 A | 7/1977 | O'Sullivan et al. | |
| 4,133,614 A * | 1/1979 | Baginski et al. | 401/206 |
| 4,304,869 A * | 12/1981 | Dyke | 435/287.6 |
| 4,444,933 A | 4/1984 | Columbus et al. | |
| 4,650,826 A | 3/1987 | Waniczek et al. | |
| 4,707,450 A | 11/1987 | Nanson | |
| 4,958,748 A | 9/1990 | Otake | |
| 5,445,462 A * | 8/1995 | Johnson et al. | 401/132 |
| 5,480,935 A | 1/1996 | Greff et al. | |
| 5,500,184 A * | 3/1996 | Palmer | 422/2 |
| 5,530,037 A | 6/1996 | McDonnell et al. | |
| 5,665,817 A | 9/1997 | Greff et al. | |
| 5,683,013 A * | 11/1997 | Morrison | 222/103 |
| 5,684,042 A | 11/1997 | Greff et al. | |
| 5,730,994 A * | 3/1998 | Askill et al. | 424/402 |
| 5,998,472 A | 12/1999 | Berger et al. | |

(Continued)

FOREIGN PATENT DOCUMENTS

FR    1075047    10/1954

OTHER PUBLICATIONS

Alexander, et al., "Development of a Safe and Effective One-Minute Preoperative Skin Preparation", *Arch. Surg.*, 120:1357-1361 (1985).

(Continued)

*Primary Examiner* — David Walczak
(74) *Attorney, Agent, or Firm* — Foley & Lardner LLP; Antoinette F. Konski

(57) ABSTRACT

An applicator for dispensing uniform thickness layers of liquid to surfaces and especially surgical sealants to surgical sites to create, in situ, a surgical incise drape is disclosed. The applicator employs a supported thin layer of foam which achieves layer thickness which are substantially independent of the pressure applied to the applicator during use. Methods of using the applicator are also disclosed.

17 Claims, 5 Drawing Sheets

U.S. PATENT DOCUMENTS

| | | | |
|---|---|---|---|
| 6,030,138 | A | 2/2000 | Losier et al. |
| 6,191,202 | B1 | 2/2001 | Greff et al. |
| 6,197,574 | B1 * | 3/2001 | Miyamoto et al. ......... 435/287.6 |
| 6,991,394 | B2 * | 1/2006 | Tufts et al. .................... 401/134 |
| 2004/0240927 | A1 | 12/2004 | Hoang et al. |

OTHER PUBLICATIONS

Chiu, et al., "Plastic Adhesive Drapes and Wound Infection After Hip Fracture Surgery" *Aust. N. Z. J. Surg.*, 63:798-801 (1993).

Hagen, et al., "A Comparison of Two Skin Preps Used in Cardiac Surgical Procedures," *AORN Journal*, 62(3):393-402 (1995).

Masterson, B., Skin Preparation, Chapter 9, in Surgical Infections, Diagnosis and Treatment, Meakins, ed., Scientific American Inc., New York, USA, publisher, pp. 119-125 (1994).

Osuna, et al., "Comparison of an Antimicrobial Adhesive Drape and Povidone-Iodine Preoperative Skin Preparation in Dogs", *Veterinary Surgery*, 21(6):458-462 (1992).

Ritter, et al., "Retrospective Evaluation of an Iodophor-Incorporated Antimicrobial Plastic Adhesive Wound Drape", *Clinical Orthopedics and Related Research*, pp. 307-308 (1988).

* cited by examiner

LIQUID APPLICATOR AND METHOD OF USE

CROSS-REFERENCE TO RELATED PATENT APPLICATIONS

This application is a An application claiming the benefit under 35 USC 119(e) U.S. Application Ser. No. 60/689,696, filed Jun. 10, 2005, incorporated herein by reference in its entirety.

FIELD OF THE INVENTION

This invention is directed to applicators and methods for applying uniform layers of liquids. More particularly, in preferred embodiments it is directed to applicators and methods for applying uniform layers of skin-adherent polymers to skin to create surgical skin sealant layers or liquid incise drapes.

REFERENCES

The following publications, patent applications and patents came to our attention:

Alexander et al., *Development of a Safe and Effective One-Minute Preoperative Skin Preparation*, Arch. Surg., 120:1357-1361 (1985).

Askill, et al., U.S. Pat. No. 5,730,994, *Methods for Draping Surgical Incision Sites*, issued Mar. 24, 1998.

Berger et al., U.S. Pat. No. 5,998,472, for *Mixed Cyanoacrylate Ester Compositions*, issued Dec. 7, 1999.

Chiu et al., *"Plastic Adhesive Drapes and Wound Infection After Hip Fracture Surgery"* Aust. N. Z. J. Surg., 63:798-801 (1993).

Columbus et al., U.S. Pat. No. 4,444,933, for *Adhesive Cyanoacrylate Compositions with Reduced Adhesion to Skin*, issued Apr. 24, 1984.

Davydov et al., U.S. Pat. No. 4,035,334, for *Medical Adhesive*, issued Jun. 12, 1977.

Greff et al., U.S. Pat. No. 5,665,817, for *Cyanoacrylate Adhesive Compositions*, issued Sep. 9, 1997.

Greff et al., U.S. Pat. No. 5,684,042, for *Cyanoacrylate Compositions Comprising an Antimicrobial Agent*, issued Nov. 3, 1997.

Greff et al., U.S. Pat. No. 6,191,202, for *Cyanoacrylate Adhesive Compositions*, issued Feb. 20, 2001.

Greff, et al., U.S. Pat. No. 5,480,935, for *Cyanoacrylate Adhesive Compositions*, issued Jan. 2, 1996.

Hagen et al., *"A Comparison of Two Skin Preps Used in Cardiac Surgical Procedures,"* AORN Journal, 62:393-402 (1995).

Halpern, U.S. Pat. No. 3,667,472, for *Adhesive for Living Tissue*, issued Jun. 6, 1972.

Hawkins and Fassett, U.S. Pat. No. 3,591,676, for *Surgical Adhesive Compositions*, issued Jul. 6, 1971.

Joyner and Coover, U.S. Pat. No. 2,784,127, for *Plasticized Monomeric Adhesive Compositions and Articles Prepared Therefrom*, issued Mar. 5, 1957.

Kronenthal et al., U.S. Pat. No. 3,995,641, for *Surgical Adhesives*, issued Dec. 7, 1976.

Masterson, *Skin Preparation*, Chapter 9, in Surgical Infections, Diagnosis and Treatment, Meakins, Ed., Scientific American, Inc., New York, USA, Publisher, pp. 119-125 (1994).

McDonnell et al., U.S. Pat. No. 5,530,037, for *Sterilized Cyanoacrylate Adhesive Composition, and a Method of Making Such a Composition*, issued Jun. 25, 1996.

O'Sullivan et al., U.S. Pat. No. 4,038,345, for *High Viscosity Cyanoacrylate Adhesive Compositions, and Process for their Preparation*, issued Jul. 26, 1977.

Osuna et al., *Comparison of an Antimicrobial Adhesive Drape and Povidone-Iodine Preoperative Skin Preparation in Dogs*, Veterinary Surgery, 21:458-462 (1992).

Otake, U.S. Pat. No. 4,958,748, for *Adhesive Container/Feeder*, issued Sep. 25, 1990.

Rabinowitz, U.S. Pat. No.3,527,224, for *Method to Surgically Bond Tissue Together*, issued Sep. 8, 1970.

Ritter et al., *Retrospective Evaluation of an Iodophor-Incorporated Antimicrobial Plastic Adhesive Wound Drape*, Clinical Orthopedics and Related Research, pp. 307-308 (1988).

Waniczek et al., U.S. Pat. No. 4,650,826, for *Stabilized Cyanoacrylate Adhesives Containing Bis-trialkylsilyl Esters of Sulfuric Acid*, issued Mar. 17, 1987.

All of the above publications, patent applications, and patents are incorporated herein by reference in their entirety.

STATE OF THE ART

Conventional surgical incise drapes include those which comprise a polymeric film coated with a pressure-sensitive adhesive. In some cases, an antimicrobial agent is incorporated directly into the adhesive to facilitate a continuous release of the antimicrobial agent onto the skin (Hagen et al., 1995; Ritter et al., 1988). After application of an antimicrobial agent onto the skin surface, the surgical incise drape is applied, adhesive side down, with pressure to affect adherence of the drape to the skin. A surgical incision is then made through the drape and the requisite surgery is performed through this incision. After completion of the surgery, the drape is conventionally removed from the skin surface.

Notwithstanding the benefits associated with current surgical incise drapes, several problems exist, which limit the general applicability of these drapes and actually increase the risk of infection. The most common and potentially serious problem associated with conventional surgical incise drapes is the separation or lifting of the drape, from the skin surface, during surgery. In one study, up to 44% of drapes experienced lifting during human surgery (Osuna et al., 1992). Alexander et al. (1985) reported a six-fold increase in infection rates in operations in which the surgical incise drape lifted away from the skin during surgery, compared to operations in which the drape did not separate from the skin.

It is known to incorporate antimicrobial agents in the plastic draping sheet or in the adhesive which is used to adhere to sheet to the surgical site. Representative antimicrobial adherent drapes are sold by 3M under the trademarks Steri-Drape and Ioban 2 Incise Film. Medical Concepts Development markets an incise film under the trademark Vi-Drape.

Askill, et al., (U.S. Pat. No.5,730,994, 1998) disclose that the use of cyanoacrylate prepolymers in the in situ formation of a cyanoacrylate polymeric drape at the surgical incision site prior to surgery overcomes many of the prior art problems associated with conventional surgical incise drapes and additionally provides incremental advantages heretofore not achieved by conventional drapes.

Greff et al. (U.S. Pat. No. 5,684,042, 1997) have demonstrated that certain iodophors can be incorporated into prepolymeric cyanoacrylate compositions to create stable film forming liquids, wherein the iodophor effectively provides for antimicrobial activity to the polymer film formed therefrom.

In these draping processes involving liquid prepolymers it is desirable that the layer of liquid prepolymer is spread quickly and evenly over the surgical site.

Foam applicators have been described for paint and adhesives. While low in cost, foam applicators of the art have presented the disadvantage of giving a coating layer of variable thickness. Generally speaking, if a foam applicator has pressure applied to it during use, its deposit is relatively thicker. If little or no pressure is applied, the layer is relatively thinner. In surgical settings a consistent thickness would be highly desirable.

STATEMENT OF THE INVENTION

The present invention is directed to an applicator for forming uniform thickness layers of liquid coatings on solid substrates. The applicator is characterized by controlling the dispensing of liquid through apertures incorporated within the applicator head. The controlled flow of liquid is passed to a thin layer of liquid-permeable open cell foam positioned over the apertures to spread the liquid into the desired uniform layer. This layer of foam is directly supported by a minimally deflectable, wide and generally flat support through which the liquid flows to the foam. The use of the thin layer of foam with the minimally deflectable direct backing support assures that the amount of liquid applied by the applicator is only minimally dependent upon the pressure applied to the foam by the user and thus that the layer thickness is substantially uniform.

While the applicator used in this invention can find use in the application of many and diverse liquids, a preferred use for this applicator is in the forming of uniform surgical incise drapes out of suitable liquid prepolymers. This use and the drapes so formed constitute additional aspects of this invention.

The applicators of this invention are additionally characterized as providing the liquids which they apply in one or more sealed containers (ampoules). These sealed containers are ruptured and the contained liquid is released for application. In the applicators of this invention, the containers are ruptured by closing together two housings and in so doing causing a focused container- breaking force to be applied to the containers within the applicator in an area adjacent to the liquid release apertures. -This focusing of the rupturing force can be accomplished by means of plates or fingers traversing along ramps or ridges which deflect the fingers to converge on the containers' sides at the point where the rupture is desired.

Thus, in one embodiment this invention provides an applicator for forming a uniform thickness layer of a liquid coating. This applicator includes:

A housing having a first end and a second end defining an inner cavity. The first end of the housing terminates in a generally flat minimally deflectable widened region with one or more liquid delivery apertures in liquid communication between the inside of the cavity and the exterior of the generally flat widened region.

A thin layer of liquid permeable-foam is conformed (stretched) over the exterior of the generally flat widened region and covering and in liquid communication with the liquid delivery apertures and affixed in that position.

One or more sealed frangible containers filled with coating liquid are contained and movable from a first position to a second position within the first housing. The first position preserves the integrity of the frangible containers and the second position is such that when the one or more containers are moved from the first position to the second position, a focused frangible-container-breaking force is applied to the containers and the coating liquid is released from the frangible containers and passes through the liquid delivery holes into the thin layer of liquid-permeable foam.

The applicator additionally includes means for moving the one or more containers from the first position to the second position. These means for moving are positioned at the second end of the first housing. These means can take the form of a second housing which slidably engages the first housing and is sized and shaped to accommodate and hold the one or more containers of liquid. In the preferred embodiments, this second housing and especially the portion of the housing which holds the one or more liquid containers includes the means for focusing the container-breaking force on the one or more containers.

In another aspect this invention provides a method for forming a substantially uniform thickness coating of a liquid coating on a substrate. This method includes the following steps:

Obtaining an applicator as just described with the coating liquid contained within the applicator's one or more frangible containers.

Moving the one or more containers from a first position to a second position within the applicator, thereby applying a focused container-breaking force to the one or more frangible containers and releasing the liquid from the containers.

Flowing the liquid from the containers and through the applicator's liquid delivery apertures to its layer of liquid-permeable foam.

Contacting the liquid-containing layer of liquid-permeable foam with the substrate and moving the applicator across the substrate in a direction generally perpendicular to the wide dimension of the generally flat widened region of the first housing of the applicator thereby causing liquid to pass through the liquid delivery apertures, through the supported thin layer of liquid-permeable foam and then to form a substantially uniform thickness layer on the substrate.

In yet another aspect this invention provides the uniform coatings, such as surgical drapes, which may be formed using this applicator and this method.

BRIEF DESCRIPTION OF THE DRAWINGS

This invention will be further described with reference to the attached drawings in which.

DESCRIPTION OF PREFERRED EMBODIMENTS

Figure 5:
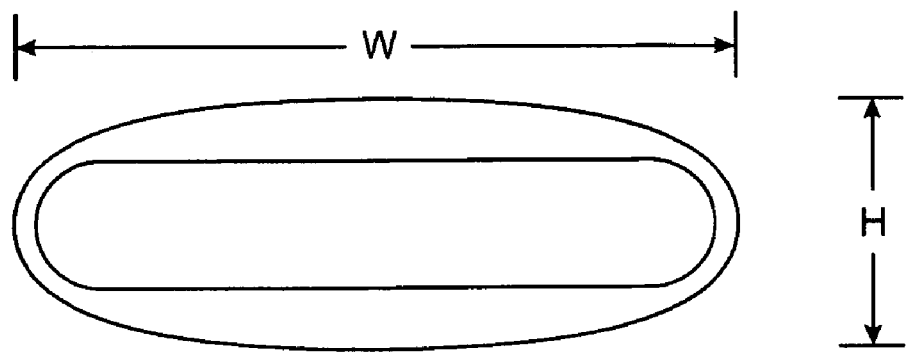
FIG. 5 is a schematic elevational view of the front portion of an applicator of this invention showing the shape of the liquid flow-spreading foam layer conformed over the relatively thin, relatively wide backing support.
Figure 6:
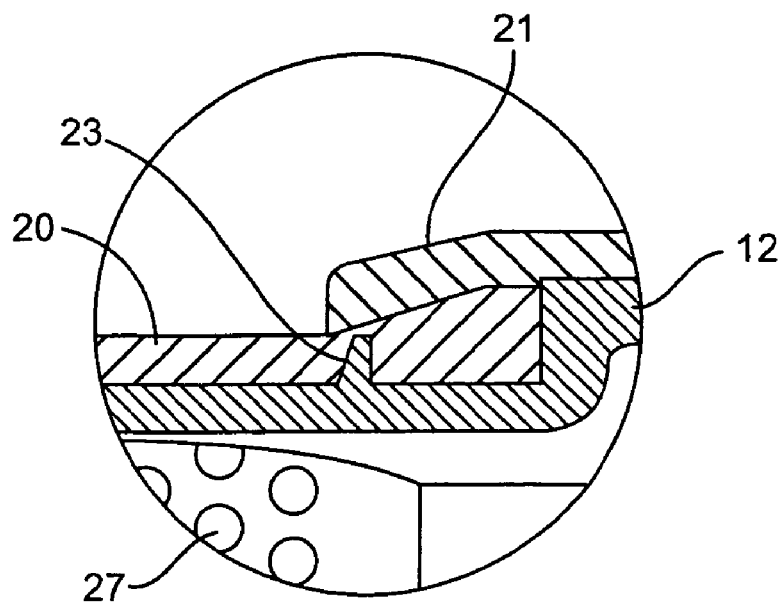
FIG. 6 is a horizontal cross-sectional view detailing the attachment of the liquid flow-spreading foam layer to the front end of the applicator.

Turning to the figures, an applicator 10 is shown. Applicator 10 includes a first housing 12. Housing 12 is typically two cooperating parts, top 12A and bottom 12B which snap together or more commonly are glued are fused into a single housing 12 during production of the application care. Housing 12 has a first ("front") end 14 and a second (opposite or "rear") end 16. First end 14 terminates in a generally flat widened region 18 having a height "H" and a width "W". As shown in FIG. 5, H and W are selected to provide an aspect ratio W:H of from about 2:1 to about 10:1 and especially from about 2.5:1 to about 8:1 and more especially from about 3:1 to about 6:1.

Figure 1:
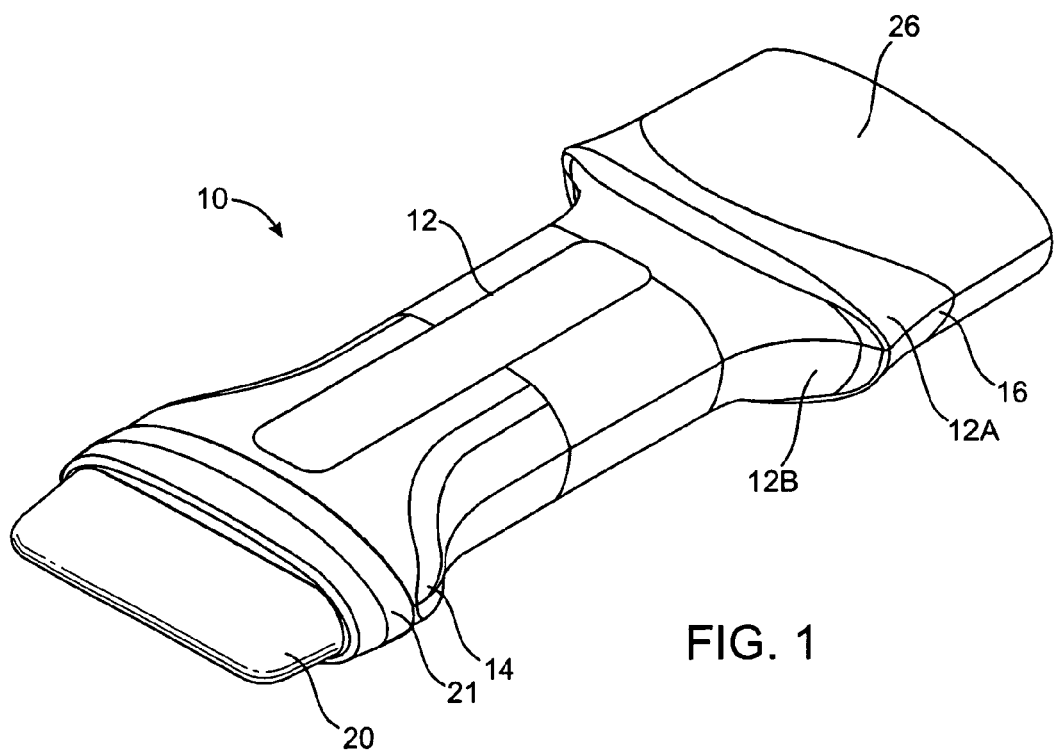
FIG. 1 is a perspective downward-looking elevational view of an applicator of this invention.
Figure 3:
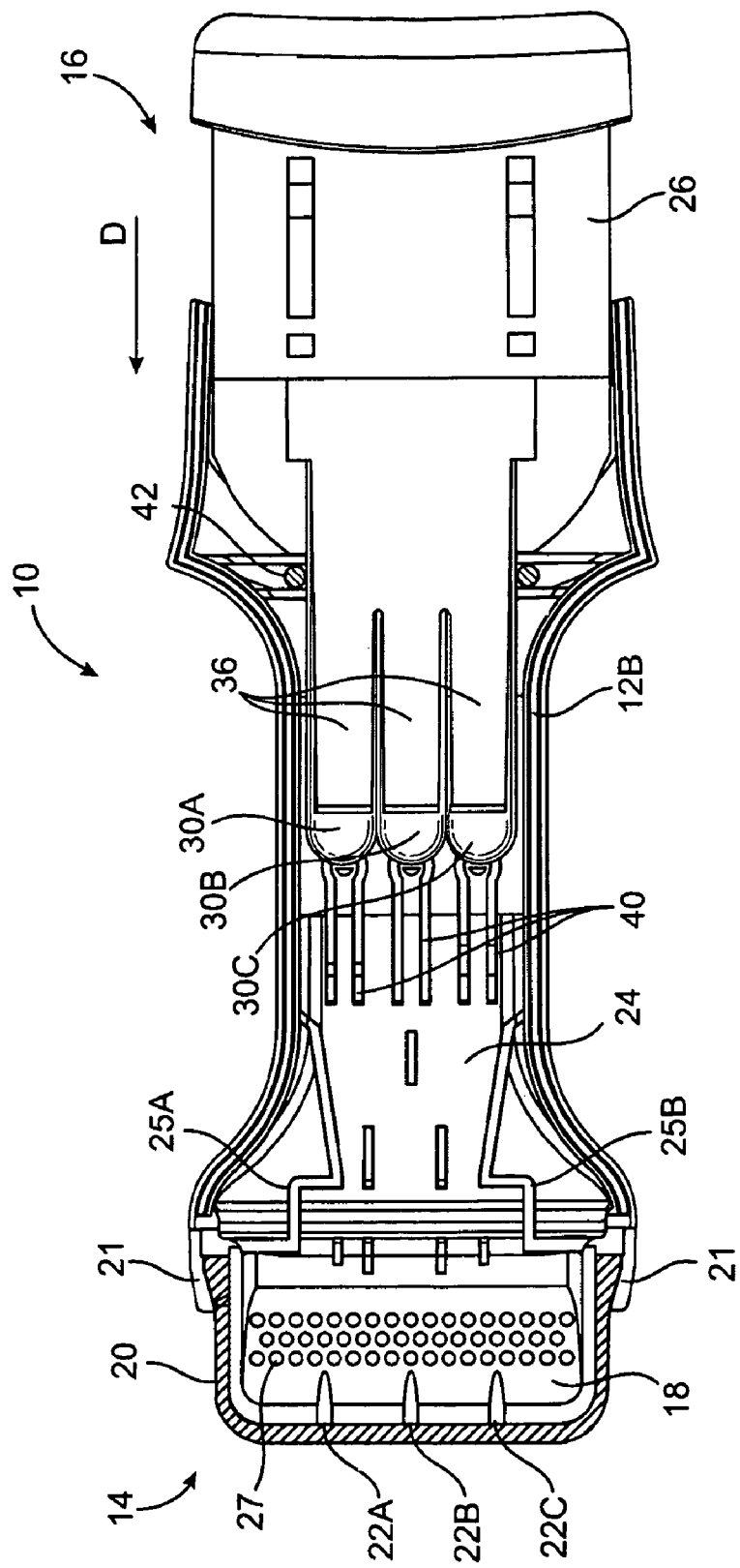
FIG. 3 is a top plan view of the applicator of FIG. 1 with the top section of its main housing removed to further show the relationship between the main housing and the movable second housing.

As shown most clearly in FIGS. 1 and 3, region 18 is covered with a conforming thin layer 20 of foam. This is a liquid-permeable (open celled) foam ranging in thickness from about 0.25 mm to about 5 mm and especially from about 0.50 mm to about 3 mm. The layer of foam may be adhered to region 18 but can also be merely conformed to exterior contours of region 18. The thin layer of foam can be molded to conform to region 18 or it can be a sheet of foam material drawn over the region 18 so as to conform to it. The layer 20 of foam may be held in place by retainer ring 21 which can also hold or assist in holding the two sections 12A and 12B of housing 12 together, if needed. Retainer teeth 23 help grip the foam layer 20 and hold it in position covering the flat area 18 at the front end 14 of the applicator.

Figure 2:
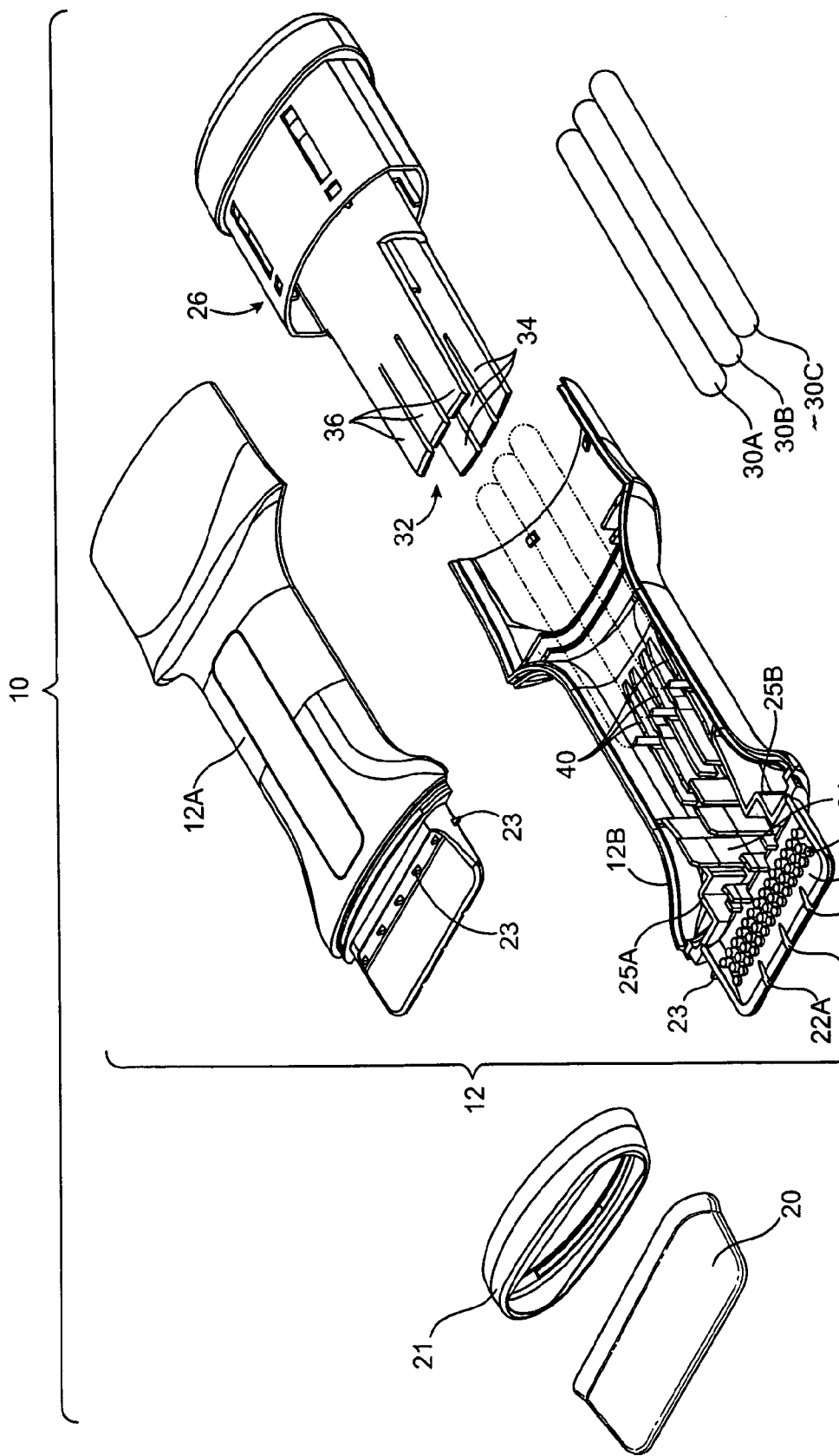
FIG. 2 is an exploded view of the applicator of FIG. 1 showing its internal structure and the working relationship among its major parts.

Region 18 is relatively rigid (minimally deflectable) and provides a firm backing for foam layer 20. In view of this relative rigidity, in use region 18 does not deflect substantially, for example more than one mm or two mm under the pressure of routine application. The first end 14 of housing 12 and its region 18 are liquid-impermeable except for the end of region 18 which contains one or more apertures (holes) 22 in liquid communication between the interior 24 of housing 12 and the foam cover 20. In FIGS. 2 and 3, three holes 22A, B and C are shown. Any number of holes such as from 2 to 10, for example, may be employed. However, it should be kept in mind that the number and size of these holes can have a flow rate-controlling effect and can control the amount of liquid passed to the foam layer 20 and applied with the applicator 10. It is generally desirable to space the holes across the width "W" of region 18 to provide a uniform flow of liquid to the foam layer across the width of the applicator. Alternatively and equivalently, a porous region at the 18 portion of the housing could provide the same liquid release function as long as the region 18 retains its relatively rigid foam-supporting properties.

The applicator includes a second housing 26 which slidably engages the second end 16 of first housing 12. As can be seen by comparing FIG. 1 and FIG. 3, second housing 26 can move relative to first housing 12 from an "open" position (FIG. 3) to a "closed" position (FIG. 1) by sliding housing 26 in direction D (See FIG. 3) relative to housing 12's fixed position. Although shown only generally in the drawings, the two housings 12 and 26 may, and in most cases will, contain various latches and detents to control their movement relative to one another. These latches and detents can serve to bias the housings into the fully open and fully closed positions so as to prevent housing 26 inadvertently separating completely from housing 12, and to prevent housing 26 prematurely moving from a fully "open" position relative to housing 12 or returning to an "open" position after the applicator has been activated by moving housing 26 to the "closed" position.

As shown in FIGS. 2 and 3, housing 12 is sized to accommodate one or more liquid containers 30A, 30B and 30C. These containers are constructed of a frangible liquid-impermeable material such as glass, brittle plastic, flexible plastic film or the like. Three containers are shown in these Figs. It will be appreciated that the present applicator will work with fewer (one or two) or more (four, five or more) containers.

Housing 26 includes a container-receiving region 32 into which the one or more liquid containers 30 are fitted. Region 32 is depicted as pairs of opposing fingers 34 and 36 which grip the one or more frangible containers 30 and hold them in place relative to housing 26.

Figure 4A:
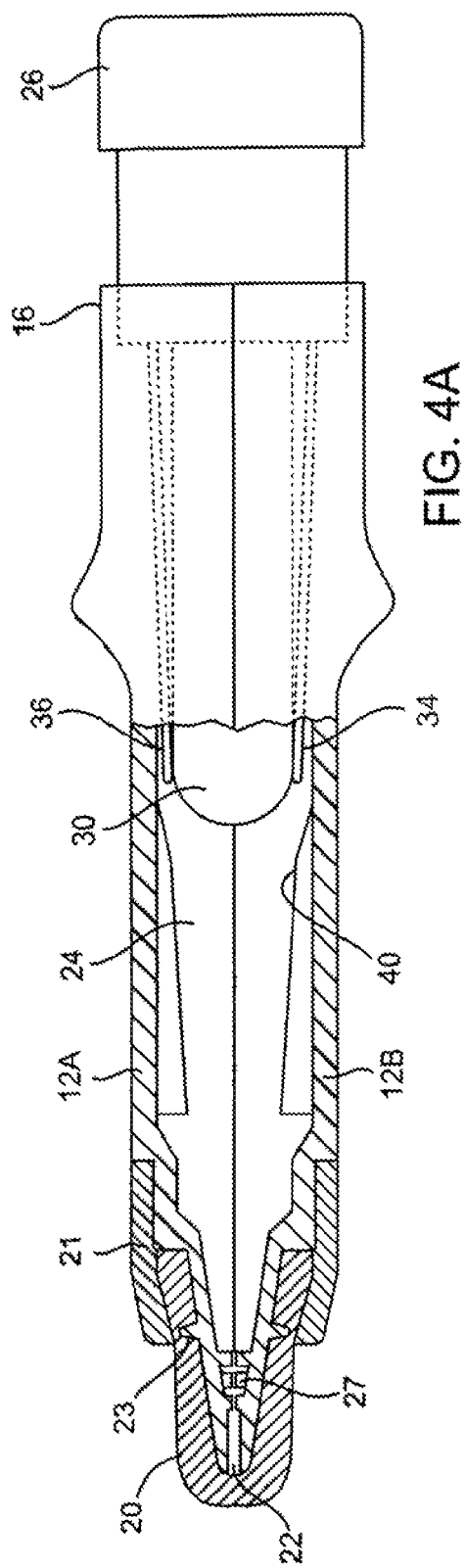
FIGS. 4A and 4B are a pair of partially cut away side elevational views of an applicator of this invention, showing the path taken by the liquid as it is released and flows from the applicator.
Figure 4B:
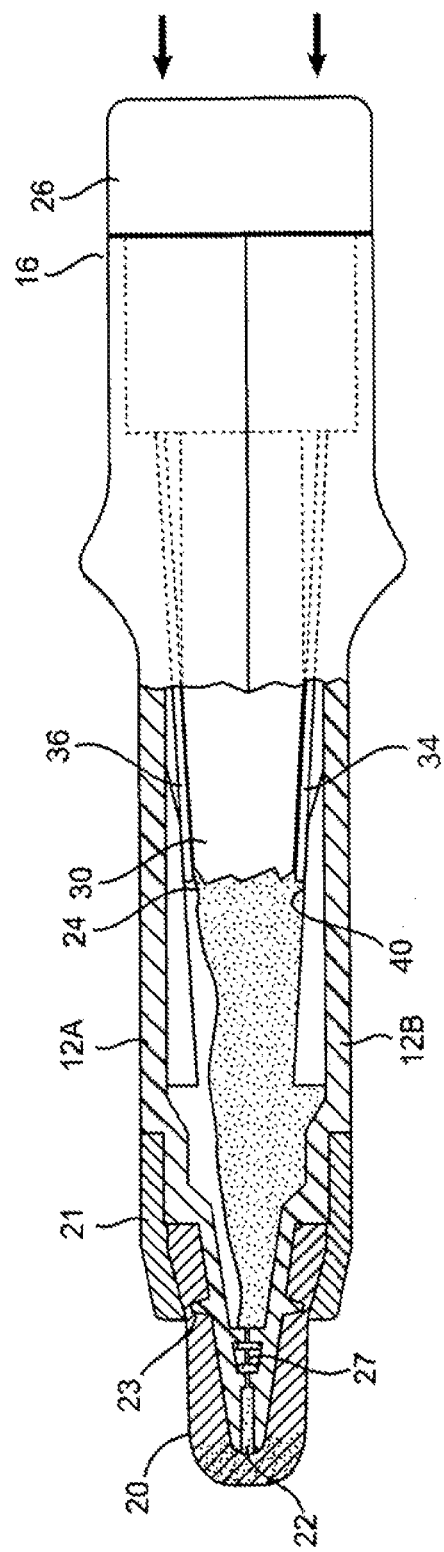

In operation, one or more containers 30 are mounted in region 32 of housing 26. Then housing 26 is slid into engagement with housing 12. In the "open" position of FIG. 4A the containers 30 are intact. To release the liquid from containers 30, housing 26 is moved in direction D, relative to housing 12. This causes containers 30 or, more preferably, fingers 34 and 36 to come into contact with ramps 40 in housing 12 and apply a container-breaking force to a predetermined region of the containers 30 and housing 26 is pushed further into housing 12 as shown in FIG. 4B.

The nature of the "container breaking" (container rupturing) will to at least some extent be a function of the material of construction of the containers. In the case of a glass or brittle plastic container, the container breaking will be a focused cracking or focused shattering of a predetermined area of the container. In the case of a flexible film container, the container breaking will be a focused puncturing or tearing or penetrating of a predetermined region of the container wall.

The rupture of the containers 30 should be predirected to occur at the first end 14 of housing 12 such that the liquid released from containers 30 can conveniently and directly enter volume 24 and pass through holes 22 to foam layer 20 for delivery to the solid substrate. The rupturing of the containers at this position can be directed by applying a focused force to the containers at the desired position of rupture with a force-focusing sharp corner, ridge, pin or projection on the ramps 40 or on one or both of fingers 34 and 36 as previously described.

The liquid released from the containers is contained within chamber 24 by walls 25A and 25B for passage through holes 22. The bottom surface of chamber 24 slopes upward toward holes 22 to create a weir. Liquid released from containers 30 passes up and over the weir. Container shards are less likely to pass over the weir and are retained in chamber 24. In addition, the flat surface of region 18 can be equipped with a series of barriers or pegs 27 which can pass liquid but hold back any shards and prevent them from being released inadvertently through holes 22. It is always a good idea to not have liquid leaking out of chamber 24 between housings 12 and 26. To that end, it is generally desirable to place a seal 42 between housing 12 and housing 26 as shown in FIG. 3 to contain the liquid within the applicator and restrict its exit to the specific exit holes 22.

APPLICATIONS

While the applicator of the invention can be used to apply consistent thickness layers of liquids in many applications, the preferred application for which it was created is the application of surgical sealants to form surgical incise drapes in situ.

The liquid materials favored for forming such surgical incise drapes are liquids containing cyanoacrylate prepolymers.

In situ polymerization of such cyanoacrylate compositions provides for an adherent polymeric film over the surgical incision site, which acts as a surgical incise drape during surgery. The adherence of the polymeric film to the skin surface is sufficiently strong to effectively preclude the possibility of lifting the drape from the skin during surgery. Additionally, the cyanoacrylate composition can be applied as a liquid to the skin surface which permits formation of an adherent film over any skin contour, including but not limited to, elbows, knees, hips, and the like.

An antimicrobially-effective amount of an antimicrobial iodophore or the like in the cyanoacrylate composition may provide significant enhancements in the effectiveness of the composition as well.

Since the polymeric film is naturally shed from the skin surface two to four days following application, there is no need to effect removal of the drape following surgery, therefore avoiding the skin trauma associated with conventional drape removal. Moreover, the addition of antimicrobial agents to the cyanoacrylate composition results in the gradual release of antimicrobial from the polymerized cyanoacrylate composition, providing antimicrobial a level protection for post-surgical infection that is currently unavailable with conventional drapes.

Accordingly, the applicator can be used in this highly desirable application for forming a surgical incision drape at a surgical incision site of a patient as follows:

(a) defining a surgical incision site of a patient;

(b) using the applicator of this invention to apply a layer of a liquid cyanoacrylate composition onto skin at the surgical incision site, which layer is consistent in thickness and of a thickness to cover the surgical incision site with the cyanoacrylate composition and (c) polymerizing this cyanoacrylate composition to form a flexible, waterproof, surgical incision drape which adheres to the surgical incision site where the cyanoacrylate composition was applied thereafter permitting the applied liquid layer to form an adherent solid surgical incise drape.

The cyanoacrylate composition which finds preferred application using the applicator of this invention comprises a cyanoacrylate ester, which, in monomeric form, is represented by formula I:

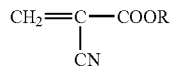

wherein R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

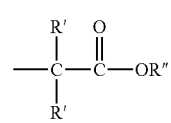

wherein each R' is independently selected from the group consisting of: hydrogen and methyl, and R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably, in the cyanoacrylate esters of formula I, R is alkyl of from 2 to 10 carbon atoms and more preferably alkyl of from 2 to 8 carbon atoms. Even more preferably, R is butyl, pentyl or octyl or a mixture of butyl and octyl (e.g., 2-ethyl-hexyl) and most preferably R is n-butyl.

In preferred embodiments, the cyanoacrylate composition may contain from about 0.01 to about 5 weight-percent antimicrobial.

In preferred embodiments, the layer of liquid cyanoacrylate laid down by the applicator has a thickness of no more that about 1 millimeter and yields a polymerized cyanoacrylate composition layer that has a thickness of no more than about 1 millimeter. More preferably, the polymer layer and the liquid layer have a uniform thickness of from about 2 to about 500 µm. Still more preferably, the layers have a thickness of from about 20 to about 100 µm.

The cyanoacrylate adhesive compositions employed in the applicator of this invention may contain, in addition to a polymerizable cyanoacrylate component and the optional antimicrobial in an amount sufficient to provide effective antimicrobial activity as already described, polymerization inhibitors, in amounts sufficient to provide inhibition or retardation of polymerization prior to the use of the composition, and/or biocompatible plasticizer components, in an amount sufficient to provide enhanced flexibility for the resulting film coating formed by polymerization of the cyanoacrylate adhesive composition.

In one version of the cyanoacrylate adhesive composition, the composition comprises:
(a) a polymerizable cyanoacrylate ester;
(b) about 0.01 to about 5 weight percent antimicrobial based on the total weight of the composition;
(c) about 100 to about 3,500 ppm of polymerization inhibitors; and
(d) optionally from about 10 to about 30 weight percent based on the total weight of the composition of a biocompatible plasticizer.

In preferred embodiments of the invention, the cyanoacrylate composition is applied onto the surface of intact skin and the incision is made subsequent to formation of the surgical incision drape. More preferably, the intact skin is further characterized as lacking pre-existing sites of infection, open wounds, scabs, sun damage, etc., which would permit the polymer to penetrate from the surface of the epidermis to or beyond the dermal layer. Notably, while these and other skin conditions may reduce the performance of the surgical drape of the instant invention, they do not necessarily preclude use of the surgical drape on such skin.

The surgical protocol in which the applicator is used preferably involves skin preparation prior to in situ formation of the cyanoacrylate polymer surgical drape over the surgical incision site. In one embodiment of the invention, the skin is cleansed to remove dirt and oils. The patient's skin may be cleansed and/or scrubbed with mild detergents, antimicrobial soaps, alcohol, or other compositions routinely used to clean wounds or prepare skin for surgery. Other cleansing or sanitizing compositions may be used, with the proviso that the cleaning and/or scrubbing compositions do not interfere with polymerization of the cyanoacrylate composition, once applied. The skin surface will typically be dried after cleansing and/or scrubbing.

The surgical incision site is optionally dried and then an adherent polymeric surgical incision drape is formed over this site by rupturing one or more containers of cyanoacrylate adhesive based sealant in an applicator of this invention and thereafter, using the applicator, applying the cyanoacrylate adhesive composition to the intact skin surface at the surgical incision site. The polymerizable cyanoacrylate prepolymers polymerize in situ to form a cyanoacrylate polymer film upon contact with the surface skin moisture, tissue protein, etc.

Polymerization occurs at ambient skin temperature while maintaining the skin surface under suitable conditions to allow polymerization to proceed. In general, the length of time required for polymerization will vary depending on factors such as the amount of adhesive composition applied, the temperature of the skin, the moisture content of the skin, the surface area of skin to which the adhesive was applied, and the like. However, polymerization is typically complete within about 10 to about 60 seconds, while the skin is maintained at ambient conditions. During this period, the patient is maintained in a position which permits the cyanoacrylate to polymerize and form a polymeric surgical incise drape, while minimizing patient movement that might dislodge the cyanoacrylate composition from that surgical incision site, or cause the cyanoacrylate composition to spread beyond the intended surgical incision site.

After polymerization, the resulting polymeric film forms a surgical incision drape which strongly adheres to the skin, is flexible and waterproof. Such strong adherence effectively eliminates the possibility that the surgical drape will lift away from the patient's skin during surgery. However, notwithstanding such strong adherence, the polymeric film defining the surgical drape will adhere to the skin for a period of about two to four days, after which time it sloughs off. This occurs because the cyanoacrylate polymer adheres only to the uppermost portion of the epidermal layer, which is continuously in the process of being sloughed off and replaced by the underlying cells. Accordingly, the cyanoacrylate surgical drape need not be removed in the manner of conventional surgical drapes, thereby eliminating the skin trauma associated with the removal of conventional surgical drapes.

It will be appreciated that while specific embodiments of this application have been described in detail this is not to be construed as limiting the scope of the invention which as defined by the appended claims.

What is claimed is:

1. An applicator for forming a uniform thickness layer of a liquid coating on a solid substrate comprising:
    a first housing having a first end and a second end and defining an inner cavity, the first end of the housing terminating in a generally flat widened region with one or more liquid delivery passages in liquid communication between the inside of the cavity and the exterior of the generally flat widened region,
    a thin layer of liquid-permeable foam conformed over the exterior of the generally flat widened region said thin layer of foam covering and in liquid communication with the liquid delivery passages and retained in that position,
    two or more sealed frangible containers filled with the coating liquid and located within a pair of opposing fingers which grip the containers inside the inner cavity and the containers movable from a first position to a second position therein, the first position preserving the integrity of the frangible containers and the second position being such that when the two or more containers are moved from the first position to the second position, a frangible-container-breaking force is applied to the containers when the pair of opposing fingers come into contact with two or more ramps each having a slope, wherein not all slopes are in parallel, and the coating liquid is released from the frangible containers and passes through the liquid delivery passages into the thin layer of liquid-permeable foam,
    a closure for sealing the second end of the first housing, and
    a movable fixture capable of moving the two or more containers from the first position to the second position within the inner cavity.

2. The applicator of claim 1 containing two or three sealed frangible containers.

3. The applicator of claim 1 wherein the fixture for moving the two or more containers is a second housing which engages the first housing and moves the two or more containers toward the first end of the first housing where they come into contact with means for applying a frangible-container-breaking pressure to them.

4. The applicator of claim 3 wherein the closure is the second housing in sealable engagement with the first housing.

5. The applicator of claim 4 wherein the sealable engagement of the first and second housings contains the liquid released from the frangible containers such that its only passage out of the first and second housings is through the liquid delivery passages.

6. The applicator of claim 1 wherein the closure is a second housing in sealable engagement with the first housing.

7. The applicator of claim 1 wherein the frangible-container-breaking force is a focused force applied to the two or more containers in a position adjacent to the liquid delivery passages.

8. The applicator of claim 7 wherein the focused force is applied to the two or more containers through force focusing means.

9. The applicator of claim 1 additionally comprising a retaining ring retaining the thin foam layer onto the exterior of the generally flat widened region of the first housing.

10. The applicator of claim 9 additionally comprising retainer teeth to grip the foam layer and hold it in position relative to the retaining ring and to the exterior of the generally flat widened region of the first housing.

11. The applicator of claim 1 wherein the generally flat widened region of the first housing has an aspect ratio (width: height) of from about 2.5:1 to about 8:1.

12. The applicator of claim 1 additionally comprising shard retainers located in the path of liquid communication between the inside of the cavity and the liquid delivery passages in the exterior of the generally flat widened region, which shard retainers are capable of retaining shards of the frangible containers within the cavity and preventing their passage through the liquid delivery passages.

13. A method for forming a substantially uniform thickness coating of a liquid coating on a substrate comprising:
    obtaining an applicator, wherein the applicator comprises:
    a first housing having a first end and a second end and defining an inner cavity, the first end of the housing terminating in a generally flat widened region with one or more liquid delivery passages in liquid communication between the inside of the cavity and the exterior of the generally flat widened region,
    a thin layer of liquid-permeable foam conformed over the exterior of the generally flat widened region said thin layer of foam covering and in liquid communication with the liquid delivery passages and retained in that position, two or more sealed frangible containers filled with the coating liquid and located within a pair of opposing fingers which grip the containers inside the inner cavity and the containers movable from a first position to a second position therein, the first position preserving the integrity of the frangible containers and the second position being such that when the two or more containers are moved from the first position to the second position, a frangible-container-breaking force is applied to the containers when the pair of opposing fingers come into contact with two or more ramps each having a slope, wherein not all slopes are in parallel, and the coating liquid is released from the frangible containers and passes through the liquid delivery passages into the thin layer of liquid-permeable foam, a closure for sealing the second end of the first housing, and a movable fixture capable of moving the two or more containers from the first position to the second position within the inner cavity, said method further comprising the steps of:

moving the containers from said first position to said second position, thereby releasing the liquid from the containers, and flowing of the liquid through the liquid delivery passages to the layer of liquid permeable foam, contacting the layer of liquid permeable foam with the substrate and moving the applicator across the substrate in a direction generally perpendicular to the wide dimension of the generally flat widened region of the first housing thereby causing liquid to pass through the liquid delivery passages, through the liquid permeable foam and then to form a substantially uniform thickness layer on the substrate.

14. The method for forming a substantially uniform thickness nonliquid polymer coating on a substrate comprising:

selecting a prepolymer solution capable of forming the desired nonliquid coating, performing the method of claim 13 with the selected prepolymer solution as the liquid contained within the two or more frangible containers, and thereafter allowing the substantially uniform thickness layer of liquid so formed to solidifying into a nonliquid polymer coating.

15. The method of claim 14 wherein the prepolymer solution comprises cyanoacrylate.

16. The method of claim 15 wherein the prepolymer solution comprises antimicrobial agent.

17. The applicator of claim 1 wherein said thin layer of liquid-permeable foam conformed over the exterior of the generally flat widened region is parallel to a longitudinal axis of the applicator.

* * * * *